(12) United States Patent
Holmes

(10) Patent No.: US 6,699,906 B2
(45) Date of Patent: Mar. 2, 2004

(54) METHOD OF ADMINISTERING LACTIC ACID SALTS TO REDUCE OR PREVENT EXERTION-RELATED MUSCLE DISCOMFORT

(76) Inventor: Carl Holmes, 118 Church St., Chagrin Falls, OH (US) 44022

( * ) Notice: Subject to any disclaimer, the term of this patent is extended or adjusted under 35 U.S.C. 154(b) by 0 days.

(21) Appl. No.: 09/950,887

(22) Filed: Sep. 10, 2001

(65) Prior Publication Data

US 2003/0050339 A1 Mar. 13, 2003

(51) Int. Cl.[7] .............................................. A61K 31/19
(52) U.S. Cl. ...................................................... 514/557
(58) Field of Search ......................................... 514/557

(56) References Cited

U.S. PATENT DOCUMENTS

| | | |
|---|---|---|
| 5,236,712 A | 8/1993 | Fregly et al. |
| 5,420,107 A | 5/1995 | Brooks |
| 5,922,765 A | 7/1999 | Fleming et al. |
| 6,039,986 A | 3/2000 | Mallangi et al. |
| 6,100,287 A | 8/2000 | Stevens et al. |

OTHER PUBLICATIONS

Langer, S., Better Nutrition for Today's Living, 54(4), p. 12(3), Apr. 1992.*

IPA AN 94:2436, Gannon, K., Drug Topics (USA), Feb. 7, 1994, 138, p. 34, abstract.*

* cited by examiner

*Primary Examiner*—Rebecca Cook
(74) *Attorney, Agent, or Firm*—Pearne & Gordon LLP

(57) ABSTRACT

A method of reducing exertion related muscle discomfort in a mammal is provided, in which a supplement containing a lactic acid salt is administered a specified period of time before exercising. A method of marketing a lactic acid salt supplement is also provided.

28 Claims, No Drawings

METHOD OF ADMINISTERING LACTIC ACID SALTS TO REDUCE OR PREVENT EXERTION-RELATED MUSCLE DISCOMFORT

TECHNICAL FIELD

This invention relates generally to nutritional supplements, and particularly to a method of administering a supplement to reduce muscle discomfort and fatigue in a mammal during exercise.

BACKGROUND OF THE INVENTION

Athletes of all levels are familiar with the muscle burn that accompanies prolonged exertion. Various causes for this phenomenon have been proposed, most of which concern metabolism of lactic acid. Formation and removal of lactic acid has been shown to be central to digestive and metabolic processes. The "Glucose Paradox" hypothesis of McGarry, which posits an indirect lactate-mediated metabolic pathway for glycogen production, and the "Lactate Shuttle" hypothesis of Brooks, which holds that lactic acid formed by contracting fast glycolytic muscle fibers acts as an energy source for slow oxidative muscle fibers, are discussed in detail in U.S. Pat. No. 5,420,107 to Brooks, which is hereby incorporated by reference in its entirety. Brooks notes that accumulation of lactic acid in the muscles causes muscle pain and interferes with contraction processes, and is a suspected cause of muscle fatigue. He therefore proposes providing a "lactic acid-like" material to athletes during exercise and recovery from exercise.

To this end Brooks administers lactic acid salts to provide beneficial nutritional supplementation during exercise and subsequent recovery. A 7% solution of 80% lactate polymer/ 20% sodium lactate in water was given to test subjects five minutes before exercise and at 20 minute intervals during exercise. Administration in this manner led to slightly reduced levels of perceived exertion as well as increased blood glucose, pH, and bicarbonate levels in test subjects over the course of exercise.

While these results are positive, it would be advantageous to administer a lactate compound in a manner to maximize positive results, reducing or eliminating exertion-related muscle discomfort, pain or burn.

SUMMARY OF THE INVENTION

A method of reducing exertion-related muscle discomfort in a mammal includes the steps of administering a dose of a lactic acid salt to the mammal effective to reduce exertion-related muscle discomfort a specified period of time before the beginning of exercise.

DETAILED DESCRIPTION OF THE PREFERRED EMBODIMENTS OF THE INVENTION

As used herein, when a preferred range such as 5–25 is given, this means preferably at least 5 and, separately and independently, preferably not more than 25. All percentages provided herein and in the claims are weight percents. As used herein and in the claims, the term "athlete" means any person who engages in exercise, the term "lactic acid salt" means any salt of lactic acid suitable for administration to a person, "exercise" means physical activity involving muscle exertion, and references to administering or administration include self-administering and self-administration.

The present invention concerns a method of reducing or eliminating exertion-related muscle discomfort in an athlete by administering a lactic acid salt. The lactic acid salt will generally be in accordance with the following formula:

$$[\text{cation}]^{+n} + CH_3CHOHCOO^-_n$$

The cation can be an inorganic ion such as calcium, sodium, potassium, ammonium, magnesium, or other biologically compatible cation. An organic cation such as an amino acid could also be used in accordance with the invention. The lactate may be present as a monomer or as a lactate polymer.

Calcium is a useful cation in connection with the invention, as it is an essential nutrient that is often under-represented in the diet. Calcium lactate (calcium-2-hydroxypropionate) may be administered either in the anhydrous form or in as a hydrate. Calcium lactate monohydrate, for example, is a preferred form in which the supplement can be administered.

Typically, the lactic acid salt supplement is prepared for conventional oral administration. The lactic acid salt may be present in pure or nearly pure form, and is preferably greater than 50% of the contents of the supplement. Oral formulations can also include such normally employed excipients as, for example, pharmaceutical grades of mannitol, lactose, starch, magnesium stearate, sodium saccharin, cellulose, magnesium carbonate, silicon dioxide and the like. These compositions may take the form of solutions, suspensions, tablets, pills, capsules, sustained release formulations, or powders.

A typical effective dose of lactic acid salt will preferably contain at least 100 mg of lactate by weight, more preferably at least 250 mg, more preferably at least 500 mg, more preferably at least 1000 mg. In a preferred embodiment, the supplement is administered orally in the form of approximately 1500 mg of calcium lactate monohydrate powder delivered in hydroxypropyl methylcellulose capsules. Doses may be larger by orders of magnitude if administered orally, as lactate is harmlessly metabolized by the body.

In order to minimize the amount of muscle discomfort, pain or burn experienced by the athlete, the lactic acid salt will preferably be administered at least 15 minutes before the beginning of exercise, more preferably at least 30 minutes before the beginning of exercise, more preferably at least 45 minutes before the beginning of exercise, more preferably at least 60 minutes before the beginning of exercise.

The exercise performed by the athlete may be any form of exercise that leads to exertion-related muscle discomfort, burn or pain. Examples include running, bicycling, skiing, and horseback riding.

It is believed that the present invention is effective not only in humans, but in mammals in general, as glucose and lactic acid metabolism pathways are fairly constant among mammals.

While not wishing to be bound by any particular theory, it is believed that administration of the lactic acid salt a significant time before the beginning of exercise achieves alkalinization of plasma and blood prior to the beginning of exercise, augmenting buffering capacity and thus extending the time before a mammal begins to sense pain from the accumulation of endogenous lactic acid produced during exertion. It also allows time for the lactate to circulate throughout the body and be absorbed by the muscles where it is most likely to be effective. Build-up of lactic acid has been proposed as a cause of muscle discomfort or burn, and metabolism of lactate to glucose by the muscles may reduce acidity levels in the muscles.

The present invention also concerns a method of marketing a lactic acid salt supplement. According to the method of marketing, at least one effective dose of lactic acid salt is offered for sale in a package bearing instructions for use. The instructions direct the user of the product to take a dose of the lactic acid salt a specified period of time before engaging in exercise. The specified period of time is at least 15 minutes, more preferably at least 30 minutes, more preferably at least 45 minutes, more preferably at least 60 minutes. The typical effective dose of lactic acid salt is described above.

Although the preferred embodiments of the invention have been shown and described, it should be understood that various modifications and changes may be resorted to without departing from the scope of the invention as disclosed and claimed herein.

What is claimed is:

1. A method of reducing exertion-related muscle discomfort in a mammal comprising administering a dose of a lactic acid salt to the mammal at least 60 minutes before the beginning of exercise to reduce exertion-related muscle discomfort.

2. The method according to claim 1, wherein the lactic acid salt comprises calcium lactate.

3. The method according to claim 2, wherein the calcium lactate salt is a hydrated calcium lactate salt.

4. The method according to claim 2, wherein the calcium lactate salt is calcium lactate monohydrate.

5. The method according to claim 1, wherein at least 100 mg of lactate are administered.

6. The method according to claim 1, wherein the lactic acid salt is administered in solid form.

7. The method according to claim 6, wherein the solid administered contains over 50% lactic acid salt.

8. The method according to claim 1, further comprising
providing a package containing at least one effective dose of said lactic acid salt, said package bearing instructions directing administration of said dose of the lactic acid salt at least 60 minutes before engaging in exercise.

9. The method according to claim 8, wherein the lactic acid salt comprises calcium lactate.

10. The method according to claim 9, wherein the calcium lactate salt is a hydrated calcium lactate salt.

11. The method according to claim 10, wherein the calcium lactate salt is calcium lactate monohydrate.

12. The method according to claim 8, wherein the dose comprises at least 100 mg of lactate.

13. The method according to claim 8, wherein the lactic acid salt is in solid form.

14. The method according to claim 13, wherein the solid contains over 50% lactic acid salt.

15. A method of reducing exertion-related muscle discomfort in a mammal comprising administering a dose of a lactic acid salt to the mammal at least 30 minutes before the beginning of exercise to reduce exertion-related muscle discomfort.

16. The method according to claim 15, said dose of said lactic acid salt being administered to said mammal at least 45 minutes before the beginning of exercise.

17. The method according to claim 15, said lactic acid salt comprising calcium lactate.

18. The method according to claim 17, said calcium lactate being a hydrated calcium lactate salt.

19. The method according to claim 17, said calcium lactate being calcium lactate monohydrate.

20. The method according to claim 15, wherein at least 100 mg of lactate are administered to said mammal.

21. The method according to claim 15, said lactic acid salt being administered in solid form.

22. The method according to claim 15, further comprising
providing a package containing at least one effective dose of said lactic acid salt, said package bearing instructions directing administration of said dose of the lactic acid salt at least 30 minutes before engaging in exercise.

23. The method according to claim 22, said instructions directing administration of said effective dose at least 45 minutes before engaging in said exercise.

24. The method according to claim 22, said lactic acid salt comprising calcium lactate.

25. The method according to claim 24, said calcium lactate being a hydrated calcium lactate salt.

26. The method according to claim 24, said calcium lactate being calcium lactate monohydrate.

27. The method according to claim 22, said effective dose being at least 100 mg of lactate.

28. The method according to claim 22, said effective dose of lactic acid salt being in solid form.

* * * * *